United States Patent [19]

Santoro

[11] Patent Number: 5,120,830
[45] Date of Patent: Jun. 9, 1992

[54] INHIBITORY PEPTIDES AGAINST $\alpha_2, \beta_1$ MEDIATED MG++ DEPENDENT ADHESION OF PLATELETS TO COLLAGEN

[75] Inventor: Samuel A. Santoro, University City, Mo.

[73] Assignee: Washington University, St. Louis, Mo.

[21] Appl. No.: 616,622

[22] Filed: Oct. 25, 1990

[51] Int. Cl.$^5$ .............. A61K 31/02; C07K 7/08; C07K 5/10
[52] U.S. Cl. ............... 50/327; 530/330; 514/14; 514/16; 514/17; 514/18
[58] Field of Search ............... 530/327; 514/14, 16, 514/18, 17

[56] References Cited
PUBLICATIONS

Staatz, et al, J. Biol. Chem. vol. 266, pp. 7363-7367, 1991.
Santoro et al., Biochem. Biophys. Res. Commun. 153, 217-223 (1988).
Kunick et al., J. Biol. Chem. 263, 4516-4519 (1988).
Staatz et al., J. Cell Biol. 108, 1917-1924 (1989).
Santoro, Cell 46, 913-920 (1986).
Coller et al., Blood 74, 182-192 (1989).
Wayner and Carter, J. Cell Biol. 105, 1873-1884 (1987).
Staatz et al., J. Biol. Chem. 265, 4778-4781 (1990).
Bornstein, Ann. Rev. Biochem. 49, 957-960 (1980).
Gulberg et al., J. Biol. Chem. 264, 12686-12694 (1989).

*Primary Examiner*—Lester L. Lee
*Assistant Examiner*—S. G. Marshall
*Attorney, Agent, or Firm*—Scott J. Meyer

[57] ABSTRACT

Novel short peptides are disclosed which are selected from the group consisting of GPAGKDGEAGAQG and fragments thereof containing the minimal sequence Ala Gly Glu Ala. These peptides have inhibitory activity against $\alpha_2\beta_1$-mediated Mg++-dependent adhesion of platelets to collagen.

4 Claims, 5 Drawing Sheets

INHIBITORY PEPTIDES AGAINST α2, β1 MEDIATED MG++ DEPENDENT ADHESION OF PLATELETS TO COLLAGEN

ACKNOWLEDGEMENT OF SUPPORT

The invention herein was made in part with government support under grant number HL40506-03 by the National Heart, Lung, and Blood Institute and by a grant from Monsanto Company.

BACKGROUND OF THE INVENTION

The present invention relates to novel inhibitory peptides and, more particularly, to short peptides which inhibit $\alpha_2\beta_1$-mediated $Mg^{++}$-dependent adhesion of platelets.

The $\alpha_2\beta_1$ integrin is electrophoretically and immunochemically identical to the platelet membrane glycoprotein Ia-IIa complex, the very late activation antigen 2 (VLA-2) on T cells, and the class II extracellular matrix receptor (ECMRII) on fibroblastic cells (1-6). The heterodimeric receptor which is composed of 160 kDa and 130 kDa polypeptides was initially characterized as a mediator of $Mg^{++}$-dependent cell adhesion to collagen (2,3,5,7-9). Recent findings indicate that whereas on platelets and fibroblasts the $\alpha_2\beta_1$ integrin serves as a collagen-specific receptor, on other cells, such as endothelial cells or melanoma cell lines, the $\alpha_2\beta_1$ integrin may exhibit a broader specificity and function as both a collagen and laminin receptor (10-13).

Several integrins, including the platelet IIb-IIIa complex ($\alpha_{IIb}\beta_3$), the vitronectin receptor ($\alpha_v\beta_3$) and the fibronectin receptor ($\alpha_5\beta_1$), recognize an arg-gly-asp (RGD) sequence within their adhesive protein ligands (14,15). The $\alpha_4\beta_1$ integrin serves as a fibronectin receptor on lymphoid cells, but recognizes a relatively short linear sequence of amino acids which does not contain the RGD sequence (16-18).

Although RGD sequences are present in collagen molecules, two lines of evidence suggest that RGD does not serve as a recognition sequence on collagen for the $\alpha_2\beta_1$ integrin. First, $Mg^{++}$-dependent platelet adhesion to collagen mediated by the $\alpha_2\beta_1$ integrin is not inhibited by peptides containing RGD sequences (7). Second, it was recently demonstrated that the $\alpha_2\beta_1$ integrin binds to the α1(I)-CB3 fragment of collagen which does not contain an RGD sequence (19).

BRIEF DESCRIPTION OF THE INVENTION

In accordance with the present invention, novel synthetic peptides are provided which inhibit $\alpha_2\beta_1$-mediated $Mg^{++}$-dependent adhesion to platelets. These novel peptides are short peptides of up to about 20 amino acid residues which contain the minimal tetrapeptide sequence Asp Gly Glu Ala (DGEA) [SEQ ID NO:3]. This tetrapeptide sequence corresponds to residues 435-438 of the α1(I) chain of type I collagen sequence.

It was found that these novel peptides effectively inhibited $\alpha_2\beta_1$-mediated $Mg^{++}$-dependent adhesion of platelets, which use the $\alpha_2\beta_1$ integrin as a collagen specific receptor, but had no effect on $\alpha_5\beta_1$-mediated platelet adhesion to fibronectin or $\alpha_6\beta_1$-mediated platelet adhesion to laminin. In contrast, with T47D breast adenocarcinoma cells, which use $\alpha_2\beta_1$ as a collagen/laminin receptor, adhesion to both collagen and laminin was inhibited by DGEA-containing peptides. Criticality of the minimal DGEA sequence [SEQ ID NO:3] for inhibitory activity is evident from the observation that deletion of the alanine residue or substitution of alanine for either the glutamic or aspartic acid residues in DGEA-containing peptides resulted in marked loss of inhibitory activity.

The adhesion of platelets to collagen plays a major role in thrombosis and hemostasis. When a blood vessel wall is damaged, platelets rapidly adhere to the exposed subendothelial components, of which fibrillar collagen is the most thrombogenic macromolecule Adherence of the platelets to fibrillar collagen results in a series of events which leads to platelet aggregation and the formation of a hemostatic plug. Accordingly, novel inhibitory peptides of the present invention are indicated as useful to medical science as it is concerned with platelet adhesion, platelet aggregation and other aspects of thrombosis and hemostasis.

The one-letter amino acid sequence of 671 residues of the α1(I) chain of type I rat collagen is available from the GenBank data bank under accession nos. AO2854 and AO2855. Its full reported sequence, minus the first 16 residues and converted to the three-letter abbreviations, is designated herein and in the accompanying Diskette as SEQ ID NO:1, and numbered from 1 to 655 in accordance with 37 CFR 1.821-825.

DETAILED DESCRIPTION OF THE INVENTION

While the specification concludes with claims particularly pointing out and distinctly claiming the subject matter regarded as forming the present invention, it is believed that the invention will be better understood from the following preferred embodiments of the invention taken in connection with the accompanying drawings in which:

FIG. 1 shows the identification of a synthetic peptide derived from the rat α1(I)-CB3 collagen peptide which inhibits the $Mg^{++}$-dependent adhesion of platelets to collagen. A) Top line represents the rat α1(I) CB3 fragment. The second and third lines indicate the relative positions of synthetic peptides employed herein within the CB3 fragment and give the number of the amino acid residues corresponding to their positions in the α1(I) collagen chain. The bottom line shows the single-letter code for the amino acid sequence of the peptide containing amino acids 430 to 442 of the rat α1(I) collagen chain. The arrow indicates the point within the 430–442 peptide that corresponds to the junction between the 403–436 and 437–466 peptides. B) The $Mg^{++}$-dependent adhesion of platelets to collagen is inhibited in a concentration dependent fashion by peptide 430–442 (○) while neither synthetic peptide 461–472 (△) nor 490–502 □ affects platelet adhesion. Data represent means of triplicate assays.

FIG. 2 is a graphical representation which shows the effects of KDGEA [SEQ ID NO:4] and structurally related peptides on the $MG^{++}$-dependent adhesion of platelets to collagen. A) Both KDGEA (○) and DGEA (■) [SEQ ID NO:3] inhibit platelet adhesion to collagen while KDGE □ [SEQ ID NO:7] does not. Control adhesion to bovine serum albumin (BSA) substrates or to collagen substrates in the presence of 2 mM EDTA was less than 0.5% in this test. B) Peptides in which either the aspartate (KAGEA,▲ [SEQ ID NO:5] or the glu (KDGAA, △) [SEQ ID NO:6] the sequence KDGEA (○) has been replaced with an ala do not inhibit Mg++-dependent adhesion of platelets to collagen. Data represent means of triplicate assays.

The novel inhibitory peptides of this invention can be prepared by known solution and solid phase peptide synthesis methods.

In conventional solution phase peptide synthesis, the peptide chain can be prepared by a series of coupling reactions in which the constituent amino acids are added to the growing peptide chain in the desired sequence. The use of various N-protecting groups, e.g., the carbobenzyloxy group or the t-butyloxycarbonyl group (BOC), various coupling reagents, e.g., dicyclohexylcarbodiimide or carbonyldimidazole, various active esters, e.g., esters of N-hydroxyphthalimide or N-hydroxy-succinimide, and the various cleavage reagents, e.g., trifluoroacetic acid (TFA), HCl in dioxane, boron tris-(trifluoracetate) and cyanogen bromide, and reaction in solution with isolation and purification of intermediates is well-know classical peptide methodology.

The preferred peptide synthesis method follows conventional Merrifield solid-phase procedures. See Merrifield, *J. Amer. Chem. Soc.* 85, 2149-54 (1963) and *Science* 150, 178-85 (1965). This procedure, though using many of the same chemical reactions and blocking groups of classical peptide synthesis, provides a growing peptide chain anchored by its carboxy terminus to a solid support, usually cross-linked polystyrene, styrenedivinylbenzene copolymer or, preferably, p-methylbenzhydrylamine polymer for synthesizing peptide amides. This method conveniently simplifies the number of procedural manipulations since removal of the excess reagents at each step is effected simply by washing the polymer.

Further background information on the established solid phase synthesis procedure can be had by reference to the treatise by Stewart and Young, "Solid Phase Peptide Synthesis," W. H. Freeman & Co., San Francisco, 1969, and the review chapter by Merrifield in *Advances in Enzymology* 32. pp. 221-296, F. F. Nold, Ed., Interscience Publishers, New York, 1969; and Erickson and Merifield, *The Proteins*, Vol. 2, p. 255 et seq. (ed. Neurath and Hill), Academic Press, New York, 1976.

In order to illustrate the invention in further detail, the following specific laboratory examples were carried out. Although specific examples are thus illustrated herein, it will be appreciated that the invention is not limited to these specific examples.

EXAMPLES

Materials and Methods

Adhesive Proteins—Type I collagen was purified from the skin of lathrytic rats as described by Bornstein and Piez (20). Human fibronectin was isolated from plasma by affinity chromatography on gelatin-Sepharose according to the method of Engvall and Ruoslahti (21). Laminin was obtained commercially from Bethesda Research Laboratories (Gaithersburg, Md.) andbovine type I collagen was from Sigma Chemical (St. Louis, Mo.).

Peptide Synthesis—Collagen peptides were made with an Applied Biosystems 430A peptide synthesizer on a p-methylbenzhydrylamine resin using double coupling cycles to ensure complete coupling at each step. Coupling was effected with preformed symmetrical anhydrides of Boc-amino acids (Applied Biosystems) and peptides were cleaved from the solid support by a hydrogen flouride procedure. Briefly, cleavage was carried out in HF and p-cresol was used at a 9/1 ratio (v/v) at 0° C. for 60 min. Peptides of 13 residues or longer were purified by successive reverse-phase chormatography on a 45×300 mm Vydac C18 column, and on a 5 μm particles, 19×150 mm microBondpak C18 column, using a gradient of 5-35% acetonitrile in 0.5% trifluoroacetic acid. For shorter peptides, a 0 to 10% acetonitrile linear gradient in 0.05% trifluoroacetic acid as applied to the same columns. The structures and purity of the synthetic peptides were verified by fast atom bombardment/mass spectroscopy and amino acid analysis.

Platelet Adhesion–Platelets were washed and labeled with $^{51}CrO_4$ as described in detail by Haverstick et al (22). Platelet adhesion to substrate composed of 0.5% BSA or 20 μg/ml of either type I collagen, laminin or fibronectin in polystryene dishes was determined as previously described in detail (7). Alternately, adhesion assays were carried out in 96 well microtiter dishes (Immulon II, Dynatech). In this case substrate coating- and adhesion assay volumes were adjusted to 100 μl and wash volumes were adjusted to 140 μl per well. Platelets were permitted to adhere for 60 min at a concentration of 1.3— to $1.8\times10^8$ platelets/ml, then wash five times in adhesion assay buffer before being lysed with two 100 ml aliquots of 2% SDS which were subsequently pooled and counted.

Cell Culture—T47D, human ductal breast adenocarcinoma cells were obtained from the American Type Culture Collection, Rockville, Md. (ATCC HTB 133) and grown in RPMI 1640 medium containing 10% fetal bovine serum and 0.2 IU insulin/ml. For use cell adhesion assay, T47D cells were labeled over night with 50 μCi/ml $^{51}CrO_4$, washed three times with ++-Mg++-free Hank's balanced salt solution (BSS) and removed from their flasks by brief treatment with 0.02% versene solution (Gibco) at 37° C. The cells were then washed with BSS, pelleted at 600×g and resuspended at $1.0\times10^5$ cells/ml in BSS containing 0.5% BSA (BSS-BSA). Aliquots were then supplemented either with 2 mM Mg++, 1 MM Mn++ and 1 mM Ca++ or with 2 mM EDTA and used in adhesion assays as described above for plateletes.

Peptide Inhibition—After labeling and washing, cells were resuspended at 2.6- to $3.6 \times 10^5$/ml for platelets or $2 \times 10^5$/ml for T47D cells. Aliquots were added to equal volumes of buffer containing appropriate concentrations of the peptides and divalent cations and preincubated for 15 min before being added to the adhesive substrates. Adhesion was quantitated as described above.

Antibody Inhibition—The P1H5 and P1D6 monoclonal antibodies directed against the $\alpha_2\beta_1$ and $\alpha_5\beta_1$ integrins respectively were generously provided by William G. Carter, Fred Hutchinson Cancer Research Center, Seattle, Wash. Cells were incubated with 10 μg/ml of antibody at room temperature for 15 min prior to use in cell adhesion assays.

RESULTS

Figure 1A:
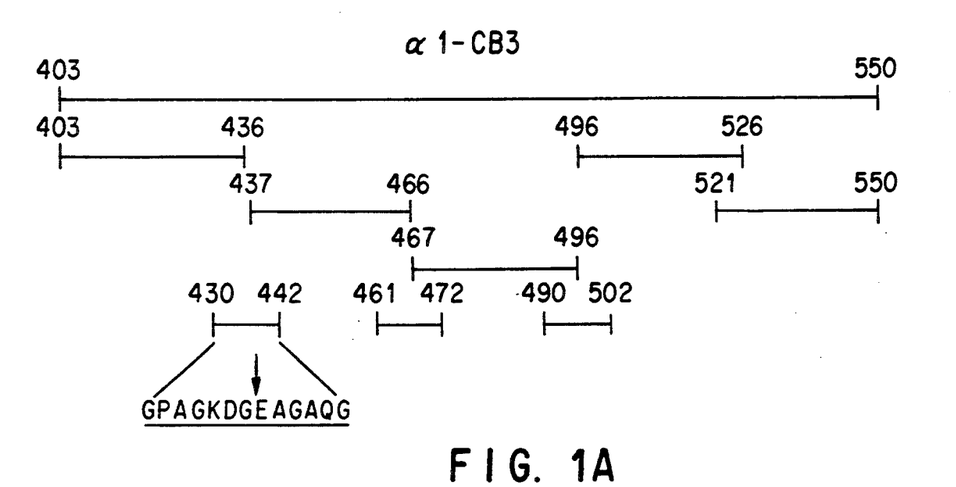

As previously reported (19), platelets adhere to the CB3 fragment of the el chain of rat type I collagen. In order to identify the specific amino acid sequence within the CB3 fragment which is recognized by the $\alpha_2\beta_1$ receptor complex, a series of five peptides were initially synthesized, each approximately 33 amino acids residues long, which together spanned the entire 148 amino acid sequence of the rat $\alpha 1(I)$-CB3 collagen fragment (FIG. 1a). These peptides were tested, both for ability to serve as solid phase adhesive substrates for the $Mg^{++}$-dependent adhesion of platelets and as fluid phase inhibitors of $Mg^{++}$-dependent platelet adhesion to intact type I collagen. None of the peptides supported the platelet adhesion nor did any peptide specifically inhibit the adhesion of platelets to collagen substrates.

While peptides spanning amino acid residues 496-526 and 521-550 of the $\alpha 1(I)$ collagen sequence shared an overlapping, common sequence of six amino acids, the junctions between the other four peptides overlapped by at most a single residue. Therefore, a second set of peptides were synthesized, 12- to 13- amino acid residues in length, which overlapped the junctions of the initial set of synthetic peptides and contained amino acid sequences corresponding to residues 430 to 442 (peptide 430), 461 to 472 (peptide 461) and 490 to 502 (peptide 490) of the rat $\alpha 1(I)$ collagen chain (FIG. 1a). These peptides were then tested for ability to inhibit $Mg^{++}$-dependent platelet adhesion to collagen.

Figure 1B:
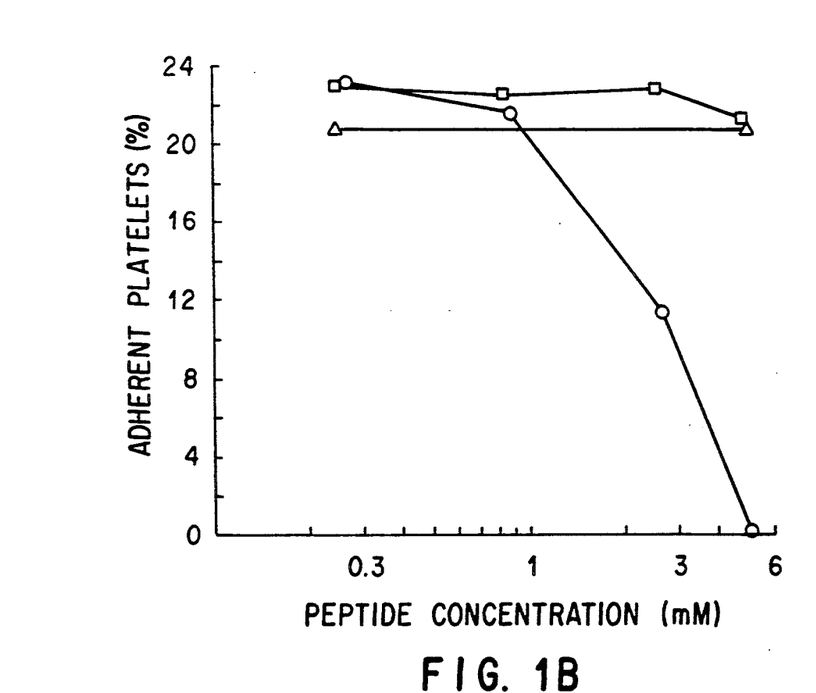

As shown in FIG. 1b, only peptide 430, namely GPAGKDGEAGAQG [SEQ ID NO:2] was capable of inhibiting platelet adhesion to collagen in a concentration-dependent manner. Half-maximal inhibition was achieved at 2.8 mM; inhibition was virtually complete at 5.4 mM. These concentrations are only slightly greater than concentrations of RGD peptides required to inhibit $\alpha_5\beta_1$-mediated cell adhesion to fibronectin. Neither peptide 461 nor 490 had any detectable inhibitory activity on platelet adhesion to collagen at comparable concentrations.

The sequence of peptide 430 is shown in the bottom line of FIG. 1A with an arrow indicating the junction between the longer peptides 403-436 and 437-466. Two striking features of this sequence are the relative lack of proline or hydroxyproline residues which contribute to the stability of the triple helical structure of collagen and the presence of the very hydrophilic sequence KDGE [SEQ ID NO:7] which was divided between the G and E residues in the 33-mer peptides. The lack of proline and hydroxyproline residues which constitute approximately 23 percent of the amino acids within type I collagen would tend to destabilize the triple helix. Puckering of the helix at this site would facilitate recognition of a linear sequence of amino acids by the $\alpha_2\beta_1$ integrin. The active sequence contained a mixture of amino- and carboxy- side chains reminiscent of those present in the RGD sequence which is known to mediate the binding of some of the other integrin receptors to their substrates (13, 14).

Figure 2A:
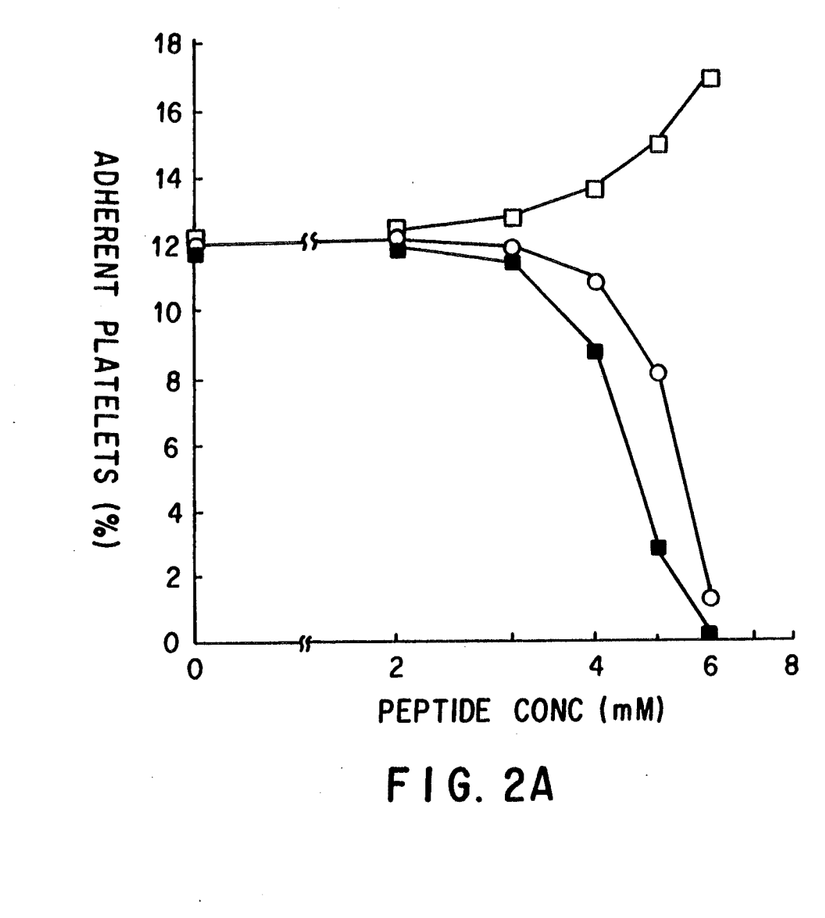

To further refine the $\alpha_2\beta_1$ recognition sequence, tetrapeptides with sequences of KDGE [SEQ ID NO:7] and DGEA [SEQ ID NO:3], as well as the pentapeptide KDGEA [SEQ ID NO:4] were synthesized. Both KDGEA and DGEA inhibited platelet adhesion to collagen at concentrations comparable to the parent peptide 430. DGEA was consistently slightly more effective than KDGEA (FIG. 2a). The peptide KDGE, which lacked the carboxy terminal alanine residue, on the other hand, was devoid of inhibitory activity and at higher concentrations tended to enhance platelet adhesion to collagen. These results indicate that while the alanine residue is needed for recognition by the $\alpha_2\beta_1$ integrin complex, the lysine residue is not.

Figure 2B:
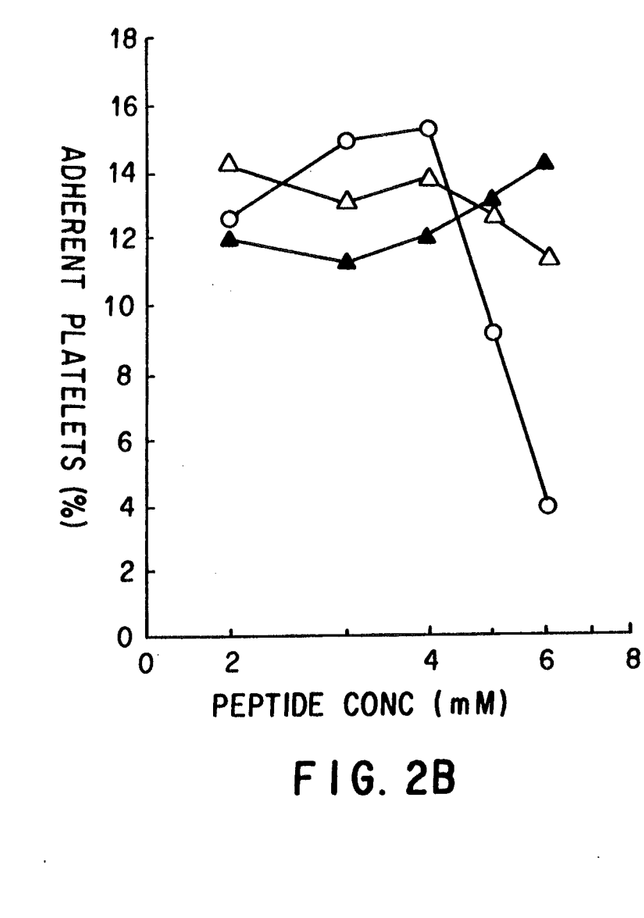

To assess the importance of the aspartate and glutamate residues in the DGEA [SEQ ID NO:3] recognition sequence, peptides with the sequences KAGEA [SEQ ID NO:5] and KDGAA [SEQ ID NO:6] were synthesized and tested for ability to inhibit $Mg^{++}$-dependent adhesion of platelets to collagen substrates. As shown in FIG. 2b, replacement of either of the acidic residues with alanine resulted in peptides lacking the ability to inhibit specifically $\alpha_2\beta_1$-mediated platelet adhesion to collagen. Thus, the DGEA sequence appears to represent the minimal recognition sequence for the $\alpha_2\beta_1$ integrin on collagen.

Figure 3:
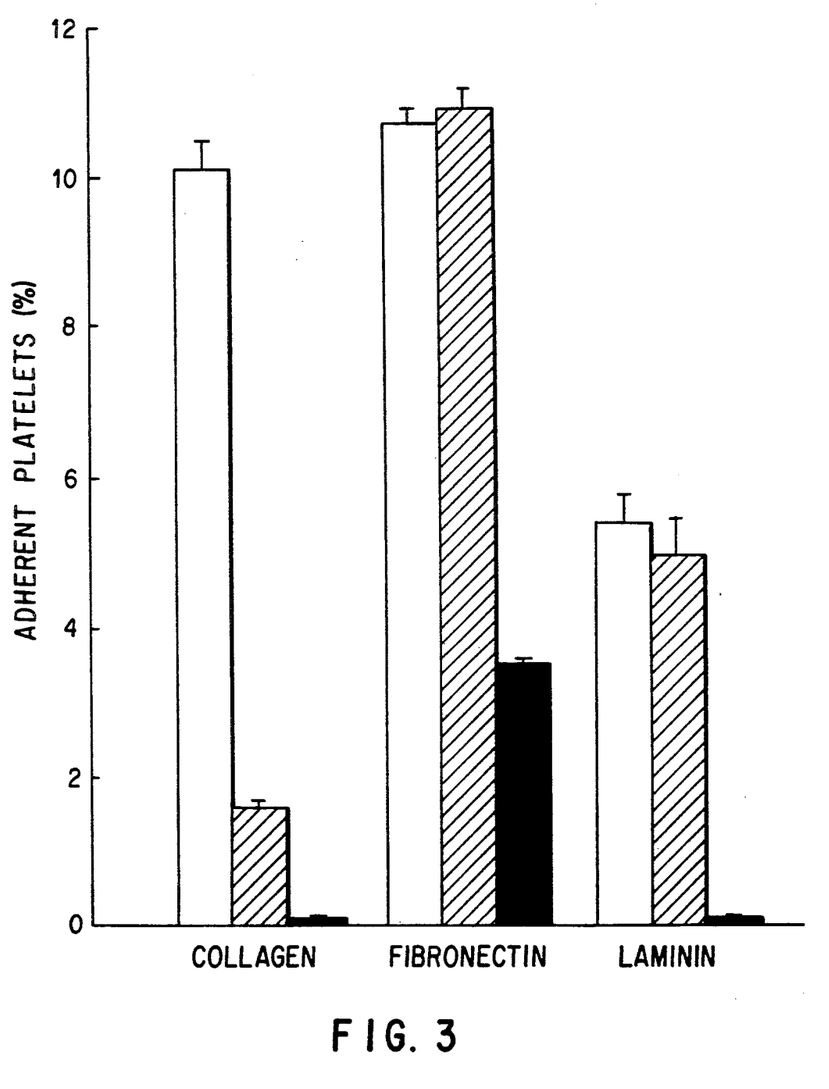
FIG. 3 is a bar chart which shows that the synthetic peptide KDGEA [SEQ ID NO: 4] inhibits the Mg++-dependent adhesion of platelets to collagen but not to fibronectin or laminin. Adhesion assays were carried out in the presence of 2 mM Mg++ (open bars), 2 mM Mg++ and 4 mM KDGEA (striped bars) or 2 mM EDTA (solid bars). Data represent means of triplicate assays and the error bars indicate one standard deviation above the mean.

It is unlikely that the DGEA [SEQ ID NO:3] sequence inhibits platelet-collagen adhesion by chelating $Mg^{++}$ ions. The inhibitory activity of KDGEA [SEQ ID NO:4] when tested in 1 mM $Mg^{++}$ was 80 percent of the activity observed in 6 mM $Mg^{++}$. To further examine the inhibitory specificity of the KDGEA [SEQ ID NO:4] peptide, the peptide was tested for ability to inhibit platelet adhesion not only to collagen, but also to fibronectin, and laminin substrates. As shown in FIG. 3, 4 mM KDGEA inhibited $Mg^{++}$-dependent platelet adhesion to collagen by 80 percent. In contrast, the adhesion of platelets to fibronectin, mediated by the $\alpha_5\beta_1$ integrin (23), and the adhesion to laminin, mediated by the $\alpha_6\beta_1$ integrin (24), were not diminished in the presence of identical concentrations of KDGEA.

It has been shown that the $\alpha_2\beta_1$ integrin complex on platelets, fibroblasts, and HT-1080 cells mediates adhesion to collagen but not to laminin (2,3,5,7-9). Recent evidence indicates that on other cell types, such as endothelial cells, keratinocytes, melanoma cell lines and other epithelial cell lines, the $\alpha_2\beta_1$ integrin exhibits a broader ligand specificity and serves as both a collagen and a laminin receptor (10-12). Monoclonal antibodies, such as P1H5 directed against the $\alpha_2\beta_1$ integrin inhibit not only adhesion to collagen, but also adhesion to laminin of these latter cell types (5,9,12).

The human breast adenocarcinoma cell line T47D, expresses high levels of the $\alpha_2 B_1$ integrin as revealed by flow cytometric analysis. As judged by the ability of the P1H5 antibody to markedly inhibit the adhesion of T47D cells to both collagen and laminin substrates (Table I), the $\alpha_2\mu_1$ integrin on T47D cells functions as a collagen/laminin receptor. The P1D6 monoclonal antibody directed against the $\alpha_5\beta_1$ integrin had no inhibitory effect on T47D adhesion to collagen or laminin (Table I).

Figure 4A:
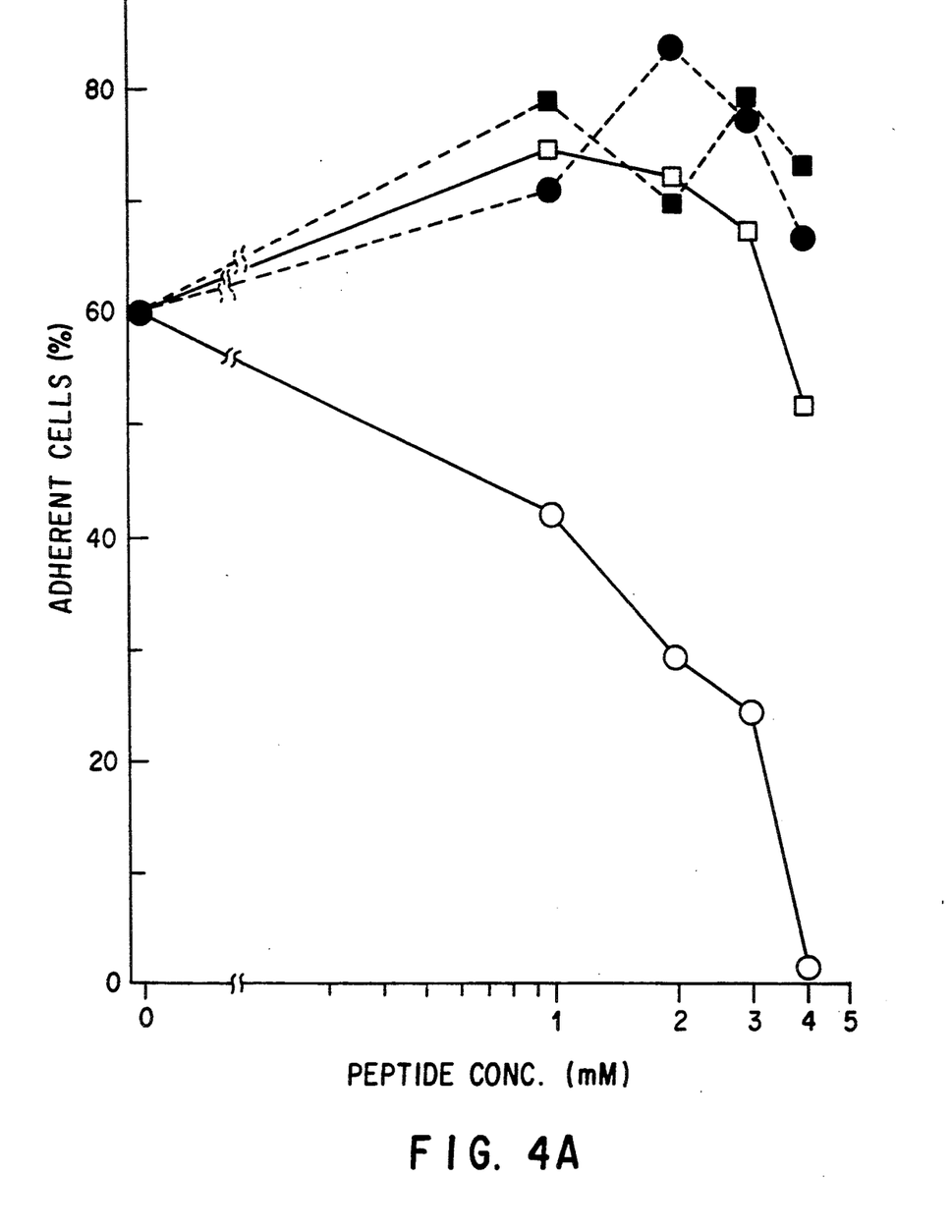
FIG. 4 is a graphical representation which shows the divalent cation-dependent adhesion of T47D carcinoma cells to collagen and laminin. Adhesion to substrates composed of either collagen (A) or laminin (B) was inhibited in a concentration dependent manner by the peptide, KDGEA (◯) [SEQ ID NO:4]. The peptides KDGE (□) [SEQ ID NO:7], KDGAA (●) [SEQ ID NO:6] and GGGGG (■) [SEQ ID NO:8] did not significantly reduce adhesion. Adhesion assays on collagen were conducted in the presence of 2 mM Mg++. Adhesion assays on laminin substrates were carried out in the presence of 2 mM Mg++, 1 mM Mn++ and 1 mM Ca++. Control adhesion assays done in the presence of 2 mM EDTA resulted in less that 1% adhesion to collagen and less than 0.5% adhesion to laminin.
Figure 4B:
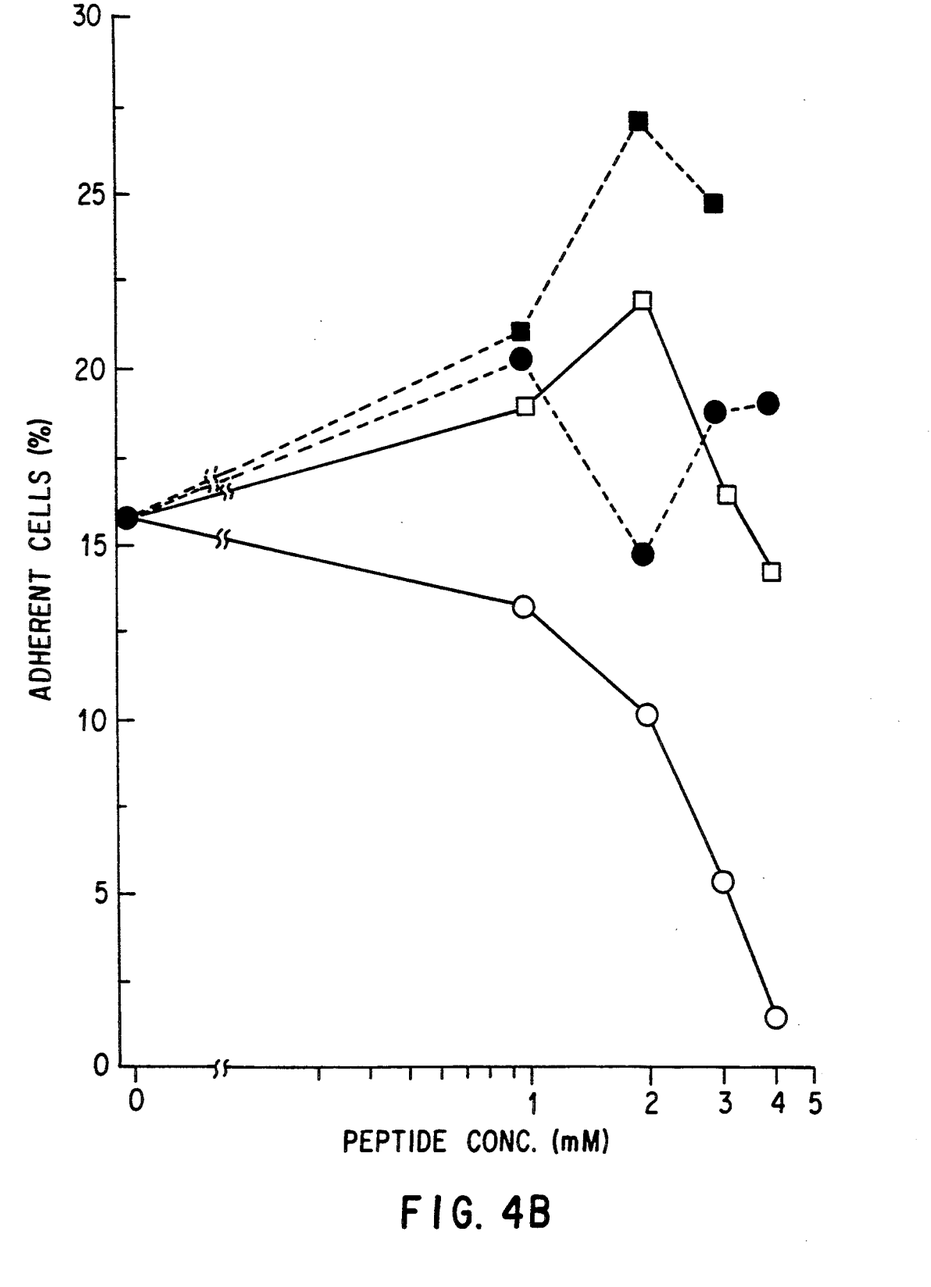

T47D cells were then used to examine the effects of KDGEA [SEQ ID NO:4] on cells which used $\alpha_2\beta_1$ as a collagen/laminin receptor. As shown in FIG. 4, KDGEA inhibited adhesion of T47D cells to both collagen and laminin substrates in a concentration dependent manner. Half-maximal inhibition on both substrates was observed at 2-2.5 mM KDGEA. The structurally related peptides KDGE [SEQ ID NO:7] and KDGAA [SEQ ID NO:6], as well as the control peptide pentaglycine showed no inhibitory activity at comparable concentrations. The specificity of the modest inhibition observed in the presence of high concentrations of these peptides could not be ascertained.

The minimal DGEA [SEQ ID NO:3] recognition sequence derived from the $\alpha1(I)$ - CB3 fragment and corresponding to residues 435-438 of the $\alpha1(I)$ chain of rat collagen is conserved in the $\alpha1(I)$ chains of other species, as well as in some, but not all, collagen chains of other types. Acceptable amino acid substitutions which might represent alternative recognition sequences in other collagenous and noncollagenous proteins remain to be elucidated.

Interestingly, the DGEA [SEQ ID NO:3] Sequence is also present at residues 54-57 of the $\alpha1(I)$ chain and at a conserved position in other chains. This location would place the second DGEA sequence within the $\alpha(I)$-CB4 fragment of type I collagen which did not support platelet adhesion in an earlier study (19). Several reasons for this apparent discrepancy may exist. The larger CB3 fragment may have bound more efficiently to the plastic surfaces than the smaller CB4 fragment. The CB3 fragment was applied to the dishes as a pure peptide, whereas the CB4 peptide was in a fraction which also contained the CB5 and CB6 fragments which could compete for binding to the plastic surface. Finally, the DGEA sequence at residues 54-57 is preceded by another aspartate residue in contrast to the DGEA sequence at residues 435-438 which is preceded by a lysine. The role of flanking sequences in ligand recognition by the $\alpha_2\beta_1$ integrin is not known.

The aforesaid data clearly indicate that DGEA-containing peptides can inhibit cell adhesion to laminin mediated by the $\alpha_2\beta_1$ integrin but not adhesion mediated by the $\alpha_2\beta_1$ integrin. Thus, the ligand recognition sites for these to laminin binding integrins are likely to differ. The DGEA sequence had not yet been identified within any laminin chains sequenced to date. The $\alpha_2\beta_1$ integrin may recognize an alternative structurally related sequence within laminin or may recognize a distinct unrelated sequence. The latter possibility is not without precedent. The platelet IIb-IIIa complex can bind both RGD peptides and an unrelated sequence from the carboxyterminus of the fibrinogen $\gamma$ chain (25,26). The peptides compete for binding to the integrin receptor and the $\gamma$ chain peptide also inhibits binding of adhesive proteins containing only the RGD recognition sequence to the receptor (27,28).

Additional studies reveal that BSA derivatized with DGEA-containing peptides support $Mg^{++}$-dependent cell adhesion which is partially inhibitable by the P1H5 monoclonal antibody directed against the $\alpha_2\beta_1$ integrin. This finding supports the role of DGEA [SEQ ID NO:3] as an $\alpha_2\beta_1$ recognition sequence.

TABLE I

T47D Cells use the $\alpha_2\beta_1$ Integrin as a Collagen/Laminin Receptor. Cells were preincubated with antibody (10 μg/ml) for 15 min prior to the determination of adhesion to collagen or laminin substrates.

| Substrate | Antibody | Integrin Specificity | Adhesion % of Cells | % of Control |
|---|---|---|---|---|
| Collagen | None | — | 19.3 ± 1.2 | 100 |
| | P1H5 | $\alpha_2\beta_1$ | 6.3 ± 1.5 | 32 |
| | P1D6 | $\alpha_5\beta_1$ | 22.2 ± 5.3 | 115 |
| Laminin | None | — | 21.7 ± 3.3 | 100 |
| | P1H5 | $\alpha_2\beta_1$ | 6.3 ± 3.7 | 29 |
| | P1D6 | $\alpha_5\beta_1$ | 25.8 ± 2.1 | 118 |

Amino acids are shown herein either by standard one letter or three letter abbreviations as follows:

| Abbreviated Designation | | Amino Acid |
|---|---|---|
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Various other examples will be apparent to the person skilled in the art after reading the present disclosure without departing from the spirit and scope of the invention. It is intended that all such other examples be included within the scope of the appended claims.

REFERENCES

1. Pischel, K. D., Bluestein, H. G., and Woods, V. L., Jr. (1988) J. Clin. Invest. 81, 505-513
2. Santoro, S. A., Rajpara, S. M., Staatz, W. D., and Woods, V. L., Jr. (1988) Biochem. Biophys. Res. Commun. 153 214-223
3. Kunicki, T. J., Nugent, D. J., Staats, S. J., Orchelowski, R. P., Wayner, E. A., and Carter, W. G. (1988) J. Biol. Chem. 262, 4516-4519
4. Takada, Y., Wayner, E. A., Carter, W. G., and Hemler, M. D. (1988) J. Cell Biochem. 37, 385-393
5. Staatz, W. D., Rajpara, S. M., Wayner, E. A., Carter, W. G., and Santoro, S. A. (1989) J. Cell Biol. 108, 1917-1924
6. Hynes, R. O. (1987) Cell 48, 549-554
7. Santoro, S. A. (1986) Cell 46, 913-920
8. Coller, B. S., Beer, J. H., Scudder, L. E., and Steinberg, M. G. (1989) Blood 74, 182-192
9. Wayner, E. A., and Carter, W. G. (1987) J. Cell Biol. 105, 1873-1884
10. Elices, M. J. and Helmer, M. E. (1989) Proc. Nat. ACAD. Sci. (U.S.A.) 89, 9906-9910
11. Languino, L. R., Gehlsen, K. R., Wayner, E. A., Carter, W. G., Engvall, E., and Ruoslahti, E. (1989) 109, 2455-2462

12. Carter, w. G., Wayner, E. A., Bouchard, T. S., and Kaur, P. (1990) *J. Cell Biol.* 110, 1287-1404
13. Kirchofer, D., Languino, L. R., Rusolahti, E., and Pierschbacher, M. D. (1990) *J. Biol. Chem.* 265, 615-618
14. Pytela, R. Pierschbacher, M. D. Ginsberg, M. G., Plow, E. F., and Ruoslahti, E. (1986) *Science* 231, 1559-1562
15. Ruoslahti, E., and Pierschbacher, M. D. (1987) *Science* 238, 491-497
16. Mould, A. P., Wheldon, L. A., Komoriya, A., Wayner, E. A., Yamada, K. M., and Humphries, M. J. (1989) *J. biol. Chem.* 265, 4020-4024
17. Wayner, E. A. Garcia-Pardo, A., Humphries, M. J., McDonald, J. A., and Carter, W. G. (1989) *J. Cell Biol.* 109, 1321-1220
18. Guan, J. -L., and Hynes, R. O. (1990) *Cell* 60, 53-61
19. Staatz, W. D., Walsh, J. J., Pexton, T. and Santoro, S. A. (1990) *J. Biol. Chem.* 265, 4778-4781
20. Bornstein, P., and Ptez, K. A. (1966) *Biochemistry* 5, 3460-3473
21. Engvall, E., and Ruoslahti, E. (1977) *Int. J. Cancer* 20, 1-15
22. Haverstick, D. M., Cowan, J. F., Yamada, K. M., and Santoro, S. A. (1985) *Blood* 66, 946-952
23. Wayner, E. A., Carter, W. G., Piotrowicz, R. S., and Kunicki, T. J. (1988) *J. Cell Biol* 107, 1881-1891
Sonnenberg, A., Modderman, P. W., and Hogervorst, F. (1988) *Nature* 336, 487-489
25. Pytela, R., Pierschbacher, M. D., Ginsberg, M. H., Plow, E. F., and Ruoslahti, E. (1986). *Science* 231, 1559-1562
26. Kloczewiak, M., Timmons, S. Lukas, T. J., and Hawiger, J. (1984) *Biochemistry* 23, 1767-1774
27. Santoro, S. A., and Lawing, W. J. (1987) *Cell* 48, 867-873
28. Plow, E. F., Srouji, A. H. Meyer, D., Morguerie, G., and Ginsberg, M. H. (1984) *J. Biol. Chem.* 259, 5388-5391

What is claimed is:

1. A peptide selected from the group consisting of GPAGKDGEAGAQG and fragments thereof containing the minimal sequence Asp Gly Glu Ala.

2. The peptide of claim 1 consisting of the tetrapeptide sequence Asp Gly Glu Ala [SEQ ID NO:3].

3. The peptide of claim 1 consisting of the pentapeptide sequence KDGEA [SEQ ID NO: 4].

4. The peptide of claim 1 consisting of the sequence GPAGKDGEAGAQG [SEQ ID NO:2].

* * * * *

UNITED STATES PATENT AND TRADEMARK OFFICE
CERTIFICATE OF CORRECTION

PATENT NO. : 5,120,830

DATED : June 9, 1992

INVENTOR(S) : Samuel A. Santoro

It is certified that error appears in the above-identified patent and that said Letters Patent is hereby corrected as shown below:

In col. 2, line 65, "0.5%" should read --0.15%--. In col. 2, line 67, after "[SEQ ID NO:6]" insert --of--. In col. 4, line 36, "as" should read --was--. In col. 6, line 68 "$\alpha_2\mu_1$" should read . In col. 8, line 49, "214" should read --217--.

Signed and Sealed this

Nineteenth Day of October, 1993

*Attest:*

BRUCE LEHMAN

*Attesting Officer*     Commissioner of Patents and Trademarks

SEQUENCE LISTING (1) GENERAL INFORMATION:
  (i) APPLICANT: Santoro, Samuel A.
  (ii) TITLE OF INVENTION: Novel Inhibitory Peptides
  (iii) NUMBER OF SEQUENCES: 8
  (iv) CORRESPONDENCE ADDRESS:
    (A) ADDRESSEE: Scott J. Meyer
    (B) STREET: 800 North Lindbergh Blvd.
    (C) CITY: St. Louis
    (D) STATE: MO
    (E) COUNTRY: USA
    (F) ZIP: 63167
  (v) COMPUTER READABLE FORM:
    (A) MEDIUM TYPE: Floppy disk
    (B) COMPUTER: IBM PC compatible
    (C) OPERATING SYSTEM: PC-DOS/MS-DOS
    (D) SOFTWARE: Patent In Release #1.24
  (vi) CURRENT APPLICATION DATA:
    (A) APPLICATION NUMBER:
    (B) FILING DATE:
    (C) CLASSIFICATION:
  (viii) ATTORNEY/AGENT INFORMATION:
    (A) NAME: Meyer, Scott J.
    (B) REGISTRATION NUMBER: 25,275
    (C) REFERENCE Ser. No.: 07/616,622
  (ix) TELECOMMUNICATION INFORMATION:
    (A) TELEPHONE: 314-694-3117
(2) INFORMATION FOR SEQ ID NO:1:
  (i) SEQUENCE CHARACTERISTICS:
    (A) LENGTH: 655 amino acids
    (B) TYPE: amino acid
    (C) TOPLOGY: linear
  (ii) MOLECULE TYPE: peptide
  (ix) FEATURE:
    (A) NAME/KEY: Peptide
    (B) LOCATION: 403..550
    (D) OTHER INFORMATION:
  (ix) FEATURE:
    (A) NAME/KEY: Peptide
    (B) LOCATION: 430..442
    (D) OTHER INFORMATION:
  (ix) FEATURE:
    (A) NAME/KEY: Peptide
    (B) LOCATION: 461..472
    (D) OTHER INFORMATION:
  (ix) FEATURE:
    (A) NAME/KEY: Peptide
    (B) LOCATION: 490..502
    (D) OTHER INFORMATION:
  (ix) FEATURE:
    (A) NAME/KEY: Peptide
    (B) LOCATION: 403..436
    (D) OTHER INFORMATION:
  (ix) FEATURE:
    (A) NAME/KEY: Peptide
    (B) Location: 437..466
    (D) OTHER INFORMATION:
  (ix) FEATURE:
    (A) NAME/KEY: Peptide
    (B) LOCATION: 467..496
    (D) OTHER INFORMATION:
  (ix) FEATURE:
    (A) NAME/KEY: Peptide
    (B) LOCATION: 496..526
    (D) OTHER INFORMATION:

(ix) FEATURE:
  (A) NAME/KEY: Peptide
  (B) LOCATION: 521..550
  (D) OTHER INFORMATION:

SEQUENCE DESCRIPTION: SEQ ID NO: 1:

| Gly | Pro | Met | Gly | Pro | Ser | Gly | Pro | Arg | Gly | Leu | Pro | Gly | Pro | Pro | Gly |
|---|---|---|---|---|---|---|---|---|---|---|---|---|---|---|---|
| 1 | | | | 5 | | | | | 10 | | | | | 15 | |

| Ala | Pro | Gly | Pro | Gln | Gly | Phe | Gln | Gly | Pro | Pro | Gly | Glu | Pro | Gly | Glu |
|---|---|---|---|---|---|---|---|---|---|---|---|---|---|---|---|
| | | | 20 | | | | 25 | | | | | 30 | | | |

| Pro | Gly | Ala | Ser | Gly | Pro | Met | Gly | Pro | Arg | Gly | Pro | Pro | Gly | Pro | Pro |
|---|---|---|---|---|---|---|---|---|---|---|---|---|---|---|---|
| | | 35 | | | | | 40 | | | | | 45 | | | |

Gly Lys Asn Gly Asp Asp Gly Glu Ala Gly Lys Pro Gly Arg Pro Gly
    50              55              60

Gln Arg Gly Pro Pro Gly Pro Gln Gly Ala Arg Gly Leu Pro Gly Thr
65              70              75              80

Ala Gly Leu Pro Gly Met Lys Gly His Arg Gly Phe Ser Gly Leu Asp
            85              90              95

Gly Ala Lys Gly Asn Thr Gly Pro Ala Gly Pro Lys Gly Glu Pro Gly
        100             105             110

Ser Pro Gly Glu Asn Gly Ala Pro Gly Gln Met Gly Pro Arg Gly Leu
        115             120             125

Pro Gly Glu Arg Gly Arg Pro Gly Pro Pro Gly Ser Ala Gly Ala Arg
    130             135             140

Gly Asp Asp Gly Ala Val Gly Ala Ala Gly Pro Pro Gly Pro Thr Gly
145             150             155             160

Pro Thr Gly Pro Pro Gly Phe Pro Gly Ala Ala Gly Ala Lys Gly Glu
            165             170             175

Ala Gly Pro Gln Gly Ala Arg Gly Ser Glu Gly Pro Gln Gly Val Arg
        180             185             190

Gly Glu Pro Gly Pro Pro Gly Pro Ala Gly Ala Ala Gly Pro Ala Gly
    195             200             205

Asn Pro Gly Ala Asp Gly Gln Pro Gly Ala Lys Gly Ala Asn Gly Ala
    210             215             220

Pro Gly Ile Ala Gly Ala Pro Gly Phe Pro Gly Ala Arg Gly Pro Ser
225             230             235             240

Gly Pro Gln Gly Pro Ser Gly Ala Pro Gly Pro Lys Gly Asn Ser Gly
            245             250             255

Glu Pro Gly Ala Pro Gly Asn Lys Gly Asp Thr Gly Ala Lys Gly Glu
            260             265             270

Pro Gly Pro Ala Gly Val Gln Gly Pro Pro Gly Pro Ala Gly Glu Glu
        275             280             285

Gly Lys Arg Gly Ala Arg Gly Glu Pro Gly Pro Ser Gly Leu Pro Gly
    290             295             300

Pro Pro Gly Glu Arg Gly Gly Pro Gly Ser Arg Gly Phe Pro Gly Ala
305             310             315             320

Asp Gly Val Ala Gly Pro Lys Gly Pro Ala Gly Glu Arg Gly Ser Pro
            325             330             335

Gly Pro Ala Gly Pro Lys Gly Ser Pro Gly Glu Ala Gly Arg Pro Gly
            340             345             350

Glu Ala Gly Leu Pro Gly Ala Lys Gly Leu Thr Gly Ser Pro Gly Ser
        355             360             365

Pro Gly Pro Asp Gly Lys Thr Gly Pro Pro Gly Pro Ala Gly Glx Asx
    370             375             380

Gly Arg Pro Gly Pro Ala Gly Pro Pro Gly Ala Arg Gly Gln Ala Gly
385             390             395             400

Val Met Gly Phe Pro Gly Pro Lys Gly Thr Ala Gly Glu Pro Gly Lys
            405             410             415

```
Ala Gly Glu Arg Gly Val Pro Gly Pro Pro Gly Ala Val Gly Pro Ala
            420             425             430

Gly Lys Asp Gly Glu Ala Gly Ala Gln Gly Ala Pro Gly Pro Ala Gly
        435             440             445

Pro Ala Gly Glu Arg Gly Glu Gln Gly Pro Ala Gly Ser Pro Gly Phe
    450             455             460

Gln Gly Leu Pro Gly Pro Ala Gly Pro Pro Gly Glu Ala Gly Lys Pro
465             470             475             480

Gly Glx Glx Gly Val Pro Gly Asp Leu Gly Ala Pro Gly Pro Ser Gly
            485             490             495

Ala Arg Gly Glu Arg Gly Phe Pro Gly Glu Arg Gly Val Gln Gly Pro
            500             505             510

Pro Gly Pro Ala Gly Pro Arg Gly Asn Asn Gly Ala Pro Gly Asx Asx
        515             520             525

Gly Ala Lys Gly Asp Thr Gly Ala Pro Gly Ala Pro Gly Ser Gln Gly
    530             535             540

Ala Pro Gly Leu Glx Gly Met Ser Gly Leu Glx Gly Pro Pro Gly Pro
545             550             555             560

Pro Gly Ser Pro Gly Glx Glx Gly Pro Ser Gly Ala Ser Gly Pro Ala
            565             570             575

Gly Pro Arg Gly Pro Pro Gly Ser Ala Gly Ser Pro Gly Lys Asx Gly
        580             585             590

Leu Asx Gly Leu Pro Gly Pro Ile Gly Pro Pro Gly Pro Arg Gly Arg
        595             600             605

Thr Gly Asx Ala Gly Pro Ser Gly Pro Pro Gly Pro Pro Gly Pro Pro
    610             615             620

Gly Pro Pro Gly Pro Pro Ser Gly Gly Tyr Asp Leu Ser Phe Phe Pro
625             630             635             640

Glx Pro Pro Glx Glx Glx Lys Ser Glx Asx Gly Gly Arg Tyr Tyr
            645             650             655
```

(2) INFORMATION FOR SEQ ID NO:2:
  (i) SEQUENCE CHARACTERISTICS:
    (A) LENGTH: 13 amino acids
    (B) TYPE: amino acid
    (D) TOPOLOGY: linear
  (ii) MOLECULE TYPE: peptide
  (xi) SEQUENCE DESCRIPTION: SEQ ID NO:2:

```
Gly Pro Ala Gly Lys Asp Gly Glu Ala Gly Ala Gln Gly
1               5               10
```

(2) INFORMATION FOR SEQ ID NO:3:
  (i) SEQUENCE CHARACTERISTICS:
    (A) LENGTH: 4 amino acids
    (B) TYPE: amino acid
    (D) TOPOLOGY: linear
  (ii) MOLECULE TYPE: peptide
  (xi) SEQUENCE DESCRIPTION: SEQ ID NO:3

```
Asp Gly Glu Ala
1
```

-continued (2) INFORMATION FOR SEQ ID NO:4:
  (i) SEQUENCE CHARACTERISTICS:
    (A) LENGTH: 5 amino acids
    (B) TYPE: amino acid
    (D) TOPOLOGY: linear
  (ii) MOLECULE TYPE: peptide
  (xi) SEQUENCE DESCRIPTION: SEQ ID NO:4:

```
Lys  Asp  Gly  Glu  Ala
1                    5
```

(2) INFORMATION FOR SEQ ID NO:5:
  (i) SEQUENCE CHARACTERISTICS:
    (A) LENGTH: 5 amino acids
    (B) TYPE: amino acid
    (D) TOPOLOGY: linear
  (ii) MOLECULE TYPE: peptide
  (xi) SEQUENCE DESCRIPTION: SEQ ID NO:5:

```
Lys  Ala  Gly  Glu  Ala
1                    5
```

(2) INFORMATION FOR SEQ ID NO:6:
  (i) SEQUENCE CHARACTERISTICS:
    (A) LENGTH: 5 amino acids
    (B) TYPE: amino acid
    (D) TOPOLOGY: linear
  (ii) MOLECULE TYPE: peptide
  (xi) SEQUENCE DESCRIPTION: SEQ ID NO:6:

```
Lys  Asp  Gly  Ala  Ala
1                    5
```

(2) INFORMATION FOR SEQ ID NO:7:
  (i) SEQUENCE CHARACTERISTICS:
    (A) LENGTH; 4 amino acids
    (B) TYPE: amino acid
    (D) TOPOLOGY: linear
  (ii) MOLECULE TYPE: peptide
  (xi) SEQUENCE DESCRIPTION: SEQ ID NO:7:

```
Lys  Asp  Gly  Glu
1
```

(2) INFORMATION FOR SEQ ID NO:8:
  (i) SEQUENCE CHARACTERISTICS:
    (A) LENGTH: 5 amino acids
    (B) TYPE: amino acid
    (D): TOPOLOGY: linear
  (ii) MOLECULE TYPE: peptide
  (xi) SEQUENCE DESCRIPTION: SEQ ID NO:8:

```
Gly  Gly  Gly  Gly  Gly
1                    5
```